United States Patent [19]

Zenk et al.

[11] Patent Number: 5,420,320

[45] Date of Patent: May 30, 1995

[54] METHOD FOR PREPARING CYCLOPENTADIENYL-TYPE LIGANDS AND METALLOCENE COMPOUNDS

[75] Inventors: Roland Zenk; Helmut G. Alt, both of Bayreuth, Germany; M. Bruce Welch; Syriac J. Palackal, both of Bartlesville, Okla.

[73] Assignee: Phillips Petroleum Company, Bartlesville, Okla.

[21] Appl. No.: 255,591

[22] Filed: Jun. 8, 1994

[51] Int. Cl.[6] .......................... C07F 17/00; C07F 7/00; C07C 1/00
[52] U.S. Cl. ........................................ 556/43; 556/53; 585/317; 585/360; 585/375
[58] Field of Search ...................... 556/43, 53; 585/317, 585/360, 375

[56] References Cited

U.S. PATENT DOCUMENTS

| | | | |
|---|---|---|---|
| 3,192,275 | 6/1965 | Freiesleben | 260/666 |
| 3,560,583 | 2/1971 | Stewart, Jr. | 260/666 |
| 3,706,541 | 12/1972 | Stourns | 44/63 |
| 4,892,851 | 1/1990 | Ewen et al. | 502/104 |
| 5,036,034 | 7/1991 | Ewen | 502/117 |
| 5,144,095 | 9/1992 | Vernier et al. | 585/20 |
| 5,158,920 | 10/1992 | Razavi | 502/152 |
| 5,191,132 | 3/1992 | Patsidis et al. | 585/375 |
| 5,210,351 | 5/1993 | Vernier et al. | 585/375 |
| 5,329,031 | 7/1994 | Miyake et al. | 556/12 |
| 5,330,948 | 7/1994 | Marks et al. | 502/104 |

OTHER PUBLICATIONS

Jutz et al., Angew. Chem., vol. 73, No. 24, p. 806 (1961).
Sturm and Hafner, "Simple Synthesis of Fulvene and Its Alkyl Derivatives", Angew. Chem. Internat. Edit., vol. 3 (1964), No. 11., p. 749.
Harter et al., "The First Heterodinuclear Complexes with Bis(cyclopentadienyl) methane Bridges", Angew. Chem. Int. Ed. Engl. 28 (1989) No. 8, pp. 1008–1009.
Harter et al., "Fulvenylsubstituierte Cp–Liganden, III. Komplexe des Anions $[C_5H_4CH-C_9H_6]^{31}$ mit Molybdan, Mangan und Rhodium", Journal of Organometallic Chemistry, 438 (1992) 297–307, JOM 22795.
Sullivan and Little, "Mono– and Dialkyltitanocene Dichlorides", J. Organometal Chem., 8 (1967) pp. 277–285.
Gaylord, "Reduction with Complex Metal Hydrides", Interscience Publishers New York, 1956, pp. 950–954 (975–98 (ref.).
Organic Syntheses, vol. 47, pp. 53–54 (1967) John Wiley and Sons, Inc., New York.
Organic Syntheses, Collective vol. 5, pp. 431–433 (1973) John Wiley and Sons, Inc. New York.

*Primary Examiner*—José G. Dees
*Assistant Examiner*—Porfirio Nazario-Gonzalez
*Attorney, Agent, or Firm*—Marianne H. Michel

[57] ABSTRACT

In accordance with the present invention there is provided a process for preparing a cyclopentadienyl-type ligand, the process comprises (1) reacting an alkali metal salt of a cyclopentadienyl-type compound and an aminofulvene compound to form a monoanion, (2) reacting the monoanion and a reducing agent to form a dianion, and (3) reacting the dianion and water to produce the cyclopentadienyl-type ligand. Another aspect of the present invention includes a process for preparing a metallocene compound comprising reacting the dianion of step (2) and a transition metal-containing compound to form the metallocene compound. Another aspect of the present invention includes a process for preparing a metallocene compound comprising reacting the ligand of step (3) and an alkali metal compound to form a dianion and then reacting the dianion with a transition metal-containing compound to form the metallocene compound.

17 Claims, No Drawings

METHOD FOR PREPARING CYCLOPENTADIENYL-TYPE LIGANDS AND METALLOCENE COMPOUNDS

The present invention relates to the preparation of cyclopentadienyl-type ligands and metallocene compounds.

BACKGROUND OF THE INVENTION

Cyclopentadienyl-type ligands have found a number of uses in the past. As used herein, the term cyclopentadienyl-type ligands includes bridged ligands containing at least two cyclopentadienyl-type groups. Cyclopentadienyl-type groups include unsubstituted cyclopentadienyl, substituted cyclopentadienyl, unsubstituted indenyl, substituted indenyl, unsubstituted fluorenyl, and substituted fluorenyl groups. Such ligands have utility in the preparation of metallocene compounds useful for the polymerization of olefins.

It would therefore be desirable to produce a variety of such ligands in pure form without byproducts and in high yields from readily available materials employing a simple and economical process. It would also be desirable to produce such ligands with a process which does not require isolation of intermediate products, i.e. a one pot process.

SUMMARY OF THE INVENTION

An object of the present invention is to provide an economical and simple process for preparing cyclopentadienyl-type ligands.

Another object of the present invention is to provide a process for preparing such ligands in pure form and high yields.

Another object of the present invention is to provide a one pot process for preparing metallocene compounds useful in the polymerization of olefins.

In accordance with the present invention there is provided a process for preparing a cyclopentadienyl-type ligand, the process comprises (1) reacting an alkali metal salt of a cyclopentadienyl-type compound, as hereinafter defined, and an aminofulvene compound to form a monoanion, (2) reacting the monoanion and a reducing agent to form a dianion, and (3) reacting the dianion and water to produce the cyclopentadienyl-type ligand. Another aspect of the present invention includes a process for preparing a metallocene compound comprising reacting the dianion of step (2) and a transition metal-containing compound. Another aspect of the present invention includes a process for preparing a metallocene compound comprising reacting the ligand of step (3) and an alkali metal compound to form an isolated dianion and then reacting the isolated dianion with a transition metal-containing compound.

DETAILED DESCRIPTION OF THE INVENTION

In the first step of the inventive process an alkali metal salt of a cyclopentadienyl-type compound is reacted with and an aminofulvene compound to form a monoanion. Cyclopentadienyl-type compounds as used herein include unsubstituted cyclopentadiene, substituted cyclopentadiene, unsubstituted indene, substituted indene, unsubstituted fluorene, and substituted fluorene. Typical substituents include hydrocarbyl groups containing 1 to 12 carbon atoms, alkoxy groups containing 1 to 12 carbon atoms, or halide. Preferably the hydrocarbyl group substituents are alkyl groups containing 1 to 10 carbon atoms, more preferably 1 to 6 carbon atoms. Some examples of substituents include methyl, ethyl, propyl, butyl, tert-butyl, isobutyl, amyl, isoamyl, hexyl, cyclohexyl, heptyl, octyl, nonyl, decyl, cetyl, 2-ethylhexyl, pentenyl, butenyl, phenyl, chloride, bromide, and iodide.

Patents disclosing the preparation of substituted cyclopentadienes include U.S. Pat. No. 3,799,994 and U.S. Pat. No. 5,144,095 the disclosures of which are incorporated herein by reference. Typical examples of substituted cyclopentadienes include methylcyclopentadiene, n-butylcyclopentadiene, di(tert-butyl)cyclopentadiene, tri(tert-butyl)cyclopentadiene, and the like.

Examples of patents disclosing the preparation of substituted indenes are U.S. Pat. No. 3,719,674 and U.S. Pat. No. 5,194,619 the disclosures of which are incorporated herein by reference. Typical examples of substituted indenes include 1-methylindene, 4,7-dimethylindene, 4-methyl-7-(1-propyl)indene, 4-ethyl-7-(1-propyl)indene, 4-methyl-7-(1-pentyl)indene, 4-ethyl-7-(1-pentyl)indene, and the like.

U.S. Pat. No. 5,191,132 and U.S. Pat. No. 5,210,352 disclose the preparation of substituted fluorenes the disclosures of which are incorporated herein by reference. Examples of substituted fluorenes include 1-methylfluorene, 4-methylfluorene, 1-tert-butylfluorene, 2-tert-butylfluorene, 4-tert-butylfluorene, 2-ethylfluorene, 2,7-dimethylfluorene, 2,7-ditert-butylfluorene, 2,7-diphenylfluorene, 2,7-dibromofluorene, 2,7-di(tert-butyl)-4-methylfluorene, 1,4-dimethylfluorene, 1,4-di(tert-butyl)fluorene, and the like.

Typically alkali metal salts of cyclopentadienyl-type compounds can be prepared by dissolving a cyclopentadienyl-type compound in a suitable liquid diluent and then adding an alkali metal compound, such as an alkali metal alkyl. Techniques of forming such salts are known in the art.

The alkali metal alkyls employed in preparing the alkali metal salt can include any alkali metal alkyls capable of forming a suitable alkali metal salt. Typically the alkali metal alkyls would be selected from the alkyls of sodium, potassium, and lithium and the alkyl group would have 1 to 8, preferably 1 to 6 carbon atoms. The preferred alkali metal alkyls are lithium alkyls. Due to availability and efficacy, butyllithium is especially preferred. In preparing the alkali metal salt, the molar ratio of the alkali metal alkyl to the cyclopentadienyl-type compound will generally be in the range of from about 1:1 to about 50:1.

Generally diluents are employed in carrying out the various steps of the present invention. Typical diluents include polar diluents such as for example tetrahydrofuran, or non-polar diluents such as alkanes, cycloalkanes, aromatic hydrocarbons, and non-cyclic ethers. Some specific examples include toluene, heptane, hexane, and diethylether.

The alkali metal salt of the cyclopentadienyl-type compound is then reacted with an aminofulvene compound to produce a monoanion. The aminofulvene compound is represented by the formula

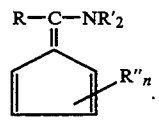

R is an alkyl group containing 1 to 20 carbon atoms, preferably 1 to 10 carbon atoms, or hydrogen. Each R' is individually selected from alkyl groups containing 1 to 20 carbon atoms, preferably 1 to 10 carbon atoms. Some examples of R and R' alkyls include methyl, ethyl, propyl, butyl, tert-butyl, isobutyl, amyl, isoamyl, hexyl, cyclohexyl, heptyl, octyl, nonyl, decyl, cetyl, and 2-ethylhexyl. Each R" is selected from the group consisting of hydrocarbyl groups containing 1 to 20 carbon atoms, preferably 1 to 10 carbon atoms, and n is 0 to 4. Some examples of R" include methyl, ethyl, propyl, butyl, tert-butyl, isobutyl, amyl, isoamyl, hexyl, cyclohexyl, heptyl, octyl, nonyl, decyl, cetyl, 2-ethylhexyl, phenyl, and phenylmethyl. The preparation of aminofulvene compounds is disclosed in U.S. Pat. No. 3,706,541 and U.S. Pat. No. 3,192,275 the disclosures of which are incorporated herein by reference.

Examples of typical aminofulvene compounds include 6-(dimethylamino)fulvene, 6-(diethylamino)fulvene, 6-(ethylmethylamino)fulvene, 6-(isopropylmethylamino)fulvene, 6-(dibutylamino)fulvene, 6-(dioctylamino)fulvene, 6-(methyloctylamino)fulvene, 1-methyl-6-(dimethylamino)fulvene, 1,2-(dimethyl)-6-(dimethylamino)fulvene, 1,2,3-(trimethyl)-6-(dimethylamino)fulvene, and 1,2,3,4-(tetramethyl)-6-(dimethylamino)fulvene. Of these compounds, 6-(dimethylamino)fulvene is preferred because it produces excellent results and is readily available.

Generally the aminofulvene compounds will be present in an amount in the range of from about 0.1 mole to about 50 moles per mole of cyclopentadienyl-type compound, preferably from about 0.2 mole to about 20 moles per mole, and more preferably from 0.5 mole to 10 moles per mole of cyclopentadienyl-type compound.

The reaction conditions for reacting the alkali metal salt of the cyclopentadienyl-type compound with the aminofulvene compound can vary broadly depending on the particular compounds employed. Generally the temperature will be in the range of from about 0° C. to about 150° C., preferably from about 0° C. to about 125° C., and more preferably from 10° C. to 100° C.

The monoanion is then reacted with a reducing agent to produce a dianion, wherein the reducing agent is selected from the group consisting of alkali metal compounds containing a hydrocarbyl group containing 1 to 20 carbon atoms, lithium aluminum hydride, and hydrogen.

Preferably the hydrocarbyl group in the alkali metal compound contains 1 to 10 carbon atoms. The alkali metal in the alkali metal compound is selected from sodium, potassium, and lithium. The preferred alkali metal compounds are lithium compounds. Examples of typical alkali metal compounds include methyllithium, ethyllithium, propyllithium, butyllithium, sec-butyllithium, phenyllithium, methylsodium, ethylsodium, propylsodium, butylsodium, phenylsodium, methylpotassium, ethylpotassium, and propylpotassium. Excellent results have been obtained with methyllithium and it is preferred.

The reducing agent will be employed in an amount in the range of from about 0.2 mole to about 50 moles per mole of monoanion, preferably from about 0.5 mole to about 20 moles per mole, and more preferably from 1 mole to 10 moles per mole of monoanion.

The reaction conditions for reacting the monoanion with the reducing agent will depend on the particular compounds employed. Generally the temperature will be in the range of from about 0° C. to about 200° C., preferably from about 10° C. to about 150° C., and more preferably from 25° C. to 150° C. Preferably the reactants and diluent will be heated at or near the reflux temperature.

The dianion can be reacted with water to produce a stable cyclopentadienyl-type ligand or can be reacted with a transition metal-containing compound to form a metallocene compound.

When reacting the dianion with water, improved yields are obtained by employing reduced temperatures and slowly combining the water and the dianion. For example, a reaction mixture of the dianion can be cooled with ice and the water added dropwise. In the alternative, the reaction mixture containing the dianion can be added dropwise to ice water. Preferably the temperature does not exceed 20° C. during this step and more preferably the temperature is less than 15° C. Typically the cyclopentadienyl-type ligand can be extracted with a solvent such as pentane, dried over sodium sulfate, and then recovered by evaporation of the solvent or recrystallization.

Generally water will be employed in an amount in the range of from about 0.2 mole to about 50 moles per mole of dianion, preferably from about 0.5 mole to about 20 moles per mole, and more preferably from 1 mole to 10 moles per mole of dianion.

The cyclopentadienyl-type ligand can be reacted with an alkali metal compound containing a hydrocarbyl group containing 1 to 20 carbon atoms to produce an isolated dianion. Alkali metal compounds employed in preparing the dianion can include any alkali metal compound capable of forming a dianion. Typically the alkali metal in the alkali metal compound would be selected from sodium, potassium, and lithium. Examples of typical alkali metal compounds include methyllithium, ethyllithium, propyllithium, butyllithium, sec-butyllithium, phenyllithium, methylsodium, ethylsodium, propylsodium, butylsodium, phenylsodium, methylpotassium, ethylpotassium, and propylpotassium. Alkali metal alkyls containing 1 to 10 carbon atoms are preferred. The preferred alkali metal compounds are lithium alkyls. Due to availability and efficacy, butyllithium alkyls are especially preferred.

Generally the alkali metal compound will be employed in an amount in the range of from about 0.2 mole to about 50 moles per mole of cyclopentadienyl-type ligand, preferably from about 0.5 mole to about 20 moles per mole, and more preferably from 1 mole to 10 moles per mole of cyclopentadienyl-type ligand.

The reaction conditions for reacting the alkali metal compound and the dianion can vary broadly depending on the particular compounds employed. Generally the temperature will be in the range of from about 0° C. to about 150° C., preferably from about 0° C. to about 125° C., and more preferably from 10° C. to 100° C.

The dianion produced before hydrolysis or the isolated dianion produced after hydrolysis, can then be reacted with a transition metal-containing compound to produce a metallocene compound. Reacting the dianion with the transition metal-containing compound before hydrolysis is especially effective when employing an alkali metal compound or hydrogen over palladium as the reducing agent. Reacting the transition metal-containing compound with the isolated dianion after hydrolysis is especially well-suited when employing lithium aluminum hydride as the reducing agent.

The transition metal-containing compound is represented by the formula $MX_x$, wherein M is a Group IVB or VB transition metal, preferably zirconium, hafnium, titanium, or vanadium, more preferably zirconium or hafnium, x is the valence of the transition metal, and each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydride. Preferably X is a halide, more preferably X is chlorine.

Some examples of such transition metal-containing compounds include, zirconium tetrachloride, zirconium tetrabromide, zirconium tetraiodide, zirconium tetramethoxide, zirconium tetraethoxide, zirconium tetrapropoxide, zirconium tetrabutoxide, hafnium tetrachloride, hafnium tetrabromide, hafnium tetraiodide, hafnium tetramethoxide, hafnium tetraethoxide, hafnium tetrapropoxide, hafnium tetrabutoxide, titanium trichloride, titanium tetrachloride, titanium tetrabromide, titanium tetraiodide, titanium tetramethoxide, titanium tetraethoxide, titanium tetrapropoxide, titanium tetrabutoxide, vanadium tetrachloride, vanadium tetraiodide, vanadium tetramethoxide, vanadium tetraethoxide, vanadium tetrapropoxide, and vanadium tetrabutoxide. Excellent results have been obtained with zirconium tetrachloride and it is preferred.

Generally the transition metal-containing compound will be present in an amount in the range of from about 0.1 mole to about 50 moles per mole of dianion, preferably from about 0.2 mole to about 20 moles per mole, and more preferably from 0.5 mole to 10 moles per mole of dianion.

The reaction conditions for reacting the dianion with the transition metal-containing compound can vary depending on the particular compounds employed. Generally the temperature will be in the range of from about 0° C. to about 150° C., preferably from about 0° C. to about 125° C., and more preferably from 10° C. to 100° C.

Examples of typical metallocene compounds which can be prepared by the inventive process include (fluorenyl)(cyclopentadienyl)methane zirconium dichloride, (fluorenyl)(cyclopentadienyl)(methyl)methane zirconium dichloride, (fluorenyl)(cyclopentadienyl)(dimethyl)methane zirconium dichloride, (fluorenyl)(cyclopentadienyl)(phenyl)methane zirconium dichloride, (1-methylfluorenyl)(cyclopentadienyl)methane zirconium dichloride, (4-methylfluorenyl)(cyclopentadienyl)methane zirconium dichloride, (1-tert-butylfluorenyl)(cyclopentadienyl)methane zirconium dichloride, (2-tert-butylfluorenyl)(cyclopentadienyl)methane zirconium dichloride, (4-tert-butylfluorenyl)(cyclopentadienyl)methane zirconium dichloride, (2-ethylfluorenyl)(cyclopentadienyl)methane zirconium dichloride, (2,7-dimethylfluorenyl)(cyclopentadienyl)methane zirconium dichloride, (2,7-di(tert-butyl)fluorenyl)(cyclopentadienyl)methane zirconium dichloride, (2,7-diphenylfluorenyl)(cyclopentadienyl)methane zirconium dichloride, (2,7-dibromofluorenyl)(cyclopentadienyl)methane zirconium dichloride, (2,7-di(tert-butyl)-4-methylfluorenyl)(cyclopentadienyl)methane zirconium dichloride, (1,4-dimethylfluorenyl)(cyclopentadienyl)methane zirconium dichloride, (1,4-di(tert-butyl)fluorenyl)(cyclopentadienyl)methane zirconium dichloride, (indenyl)(cyclopentadienyl) zirconium methane dichloride, (indenyl)(cyclopentadienyl)(methyl)methane zirconium dichloride, (indenyl)(cyclopentadienyl)(dimethyl)methane zirconium dichloride, (indenyl)(cyclopentadienyl)(phenyl)methane zirconium dichloride, (4,7-dimethylindenyl)(cyclopentadienyl)methane zirconium dichloride, (4,7-dimethylindenyl)(cyclopentadienyl)(methyl)methane zirconium dichloride, (4,7-dimethylindenyl)(cyclopentadienyl)(dimethyl)methane zirconium dichloride, (4,7-dimethylindenyl)(cyclopentadienyl)(phenyl)methane zirconium dichloride, (4-methyl-7-(1-propyl)indenyl)-(cyclopentadienyl)methane zirconium dichloride, (4-methyl-7-(1-propyl)indenyl)(cyclopentadienyl)(methyl)methane zirconium dichloride, (4-methyl-7-(1-propyl)indenyl)(cyclopentadienyl)(dimethyl)methane zirconium dichloride, (4-methyl-7-(1-propyl)indenyl)-(cyclopentadienyl)(phenyl)methane zirconium dichloride, (4-methyl-7-(1-pentyl)indenyl)(cyclopentadienyl)methane zirconium dichloride, (4-methyl-7-(1-pentyl)indenyl)(cyclopentadienyl)(methyl)methane zirconium dichloride, (4-methyl-7-(1-pentyl)indenyl)(cyclopentadienyl)(dimethyl)methane zirconium dichloride, (4-methyl-7-(1-pentyl)indenyl)(cyclopentadienyl)(phenyl)methane zirconium dichloride, bis(cyclopentadienyl)methane zirconium dichloride, bis(cyclopentadienyl)(methyl)methane zirconium dichloride, bis(cyclopentadienyl)(dimethyl)methane zirconium dichloride, bis(cyclopentadienyl)(phenyl)methane zirconium dichloride, bis(cyclopentadienyl)methane zirconium dibromide, bis(cyclopentadienyl)methane zirconium diiodide, bis(methylcyclopentadienyl)methane zirconium dichloride, bis(n-butylcyclopentadienyl)methane zirconium dichloride, bis(cyclopentadienyl)methane hafnium dichloride, bis(cyclopentadienyl)methane hafnium dibromide, bis(cyclopentadienyl)methane hafnium diiodide, bis(methylcyclopentadienyl)methane hafnium dichloride, bis(n-butylcyclopentadienyl)methane hafnium dichloride, bis(cyclopentadienyl)methane titanium dichloride, bis(methylcyclopentadienyl)methane titanium dichloride, bis(n-butylcyclopentadienyl)methane titanium dichloride, bis(cyclopentadienyl)methane zirconium methyl chloride, bis(methylcyclopentadienyl)methane zirconium ethyl chloride, bis(n-butylcyclopentadienyl)methane zirconium phenyl chloride, bis(cyclopentadienyl)methane hafnium methyl chloride, bis(methylcyclopentadienyl)methane hafnium ethyl chloride, bis(n-butylcyclopentadienyl)methane hafnium phenyl chloride, bis(cyclopentadienyl)methane titanium methyl chloride, bis(methylcyclopentadienyl)methane titanium ethyl chloride, bis(n-butylcyclopentadienyl)methane titanium phenyl chloride, bis(cyclopentadienyl)methane zirconium dimethyl, bis(methylcyclopentadienyl)methane zirconium dimethyl, bis(n-butylcyclopentadienyl)methane zirconium dimethyl, bis(cyclopentadienyl)methane hafnium dimethyl, bis(methylcyclopentadienyl)methane hafnium dimethyl, bis(n-butylcyclopentadienyl)methane hafnium dimethyl, bis(cyclopentadienyl)methane titanium dimethyl, bis(methylcyclopentadienyl)methane titanium dimethyl, bis(n-butylcyclopentadienyl) methane titanium dimethyl, bis(pentamethylcyclopentadienyl)methane titanium diphenyl, and the like.

Generally, organoaluminoxane cocatalysts are employed with the metallocene compounds to produce a catalyst system. Various techniques are known for making organoaluminoxanes. One technique involves the controlled addition of water to a trialkylaluminum. Another technique involves combining a trialkylaluminum and a hydrocarbon with a compound containing water of adsorption or a salt containing water of crystallization. Many suitable organoaluminoxanes are commercially available.

Typically the organoaluminoxanes comprise oligomeric, linear and/or cyclic hydrocarbyl aluminoxanes having repeating units of the formula

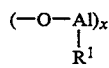

wherein each $R^1$ is a hydrocarbyl group, preferably an alkyl group containing 1–8 carbon atoms, x is 2 to 50, preferably 4 to 40, more preferably 10 to 40. Typically $R^1$ is predominantly methyl or ethyl. Preferably at least about 30 mole percent of the repeating groups have an $R^1$ which is methyl, more preferably at least 50 mole percent, and still more preferably at least 70 mole percent. Generally in the preparation of an organoaluminoxane, a mixture of linear and cyclic compounds is obtained. Organoaluminoxanes are commercially available in the form of hydrocarbon solutions, generally aromatic hydrocarbon solutions.

A solid organoaluminoxy product can be prepared by reacting an organoaluminoxane and an oxygen-containing compound selected from the group consisting of organo boroxines, organic boranes, organic peroxides, alkylene oxides, and organic carbonates. Organo boroxines are preferred.

The amount of organoaluminoxane relative to the metallocene compound can vary broadly depending upon the particular catalyst selected and the results desired. Typically, the organoaluminoxane will be present in the amount of about 0.1 mole to about 10,000 moles per mole of metallocene compound, preferably about 5 moles to about 5,000 moles, and more preferably 10 moles to 5,000 moles.

A variety of olefin compounds are suitable for use as monomers in the polymerization process of the present invention. Olefins which can be employed include aliphatic mono-1-olefins. While the invention would appear to be suitable for use with any aliphatic mono-1-olefin, those olefins having 2 to 18 carbon atoms are most often used. Ethylene and propylene are especially preferred. Often a second mono-1-olefin (comonomer) having from 3 to 12 carbon atoms, preferably from 4 to 10 carbon atoms can be employed. Preferred comonomers include 1-butene, 1-pentene, 4-methyl-1-pentene, 1-hexene, 1-heptene, 1-octene, and mixtures thereof. Of these 1-hexene is most preferred.

The polymerization processes according to the present invention can be performed by any known method and can be conducted either batchwise or continuously. The olefin, metallocene compound, and organoaluminoxane can be contacted in any order. A diluent such as isobutane is generally employed. The reactor is heated to the desired reaction temperature and olefin, such as ethylene, is then admitted and maintained at a partial pressure within a range of from about 0.5 MPa to about 5.0 MPa (70–725 psi) for best results. At the end of the designated reaction period, the polymerization reaction is terminated and the unreacted olefin and diluent can be vented. The reactor can be opened and the polymer can be collected as a free-flowing white solid and dried to obtain the product.

The reaction conditions for contacting the olefin and the catalyst system can vary broadly depending on the olefin employed, and are those sufficient to polymerize the mono-1-olefins. Generally the temperature is in the range of about 20° C. to about 300° C., preferably in the range of 50° C. to 150° C. The pressure is generally in the range of from about 0.5 MPa to about 10.0 MPa (70–1500 psi).

The following examples will serve to show the present invention in detail by way of illustration and not by way of limitation.

EXAMPLES

Examples 1–3 demonstrate the effectiveness of the inventive process in preparing cyclopentadienyl-type ligands. Example 4 demonstrates the preparation of a metallocene compound useful as a catalyst.

Example 1

The cyclopentadienyl-type ligand, (fluorenyl)(cyclopentadienyl)methane was prepared as follows. A solution of 13.72 g (0.08252 mol) fluorene in 150 mL tetrahydrofuran (THF) was treated with 51.6 mL (0.08252 moles) 1.6M n-butyllithium solution at room temperature. The mixture was stirred at room temperature for 6 hours and then 10.00 g (0.0825 moles) 6-(dimethylamino)fulvene suspended in 50 mL THF were added and this mixture was stirred for 16 hours. The mixture was then reacted with 6.27 g (0.1652 mol) $LiAlH_4$ and refluxed 5.5 hours. The product was carefully hydrolysed with ice water, 500 mL ether, and HCl. Then the clear phase was separated and was extracted with ether, dried over sodium sulfate, and the solvent was evaporated at 15° C. The solid crude product was mixed with pentane, filtered over silica gel, concentrated in vacuo, and cooled to $-10°$ C. to $-25°$ C. to produce light yellow crystals. After a second recrystallization from pentane, the yield was 5.27 g (fluorenyl)(cyclopentadienyl)methane, or 88 percent. Gas chromatography (GC) analysis indicated 97 percent purity.

Example 2

A second batch of the cyclopentadienyl-type ligand, (fluorenyl)(cyclopentadienyl)methane was prepared as follows. A solution of 13.7 g (0.0824 moles) fluorene in 200 mL tetrahydrofuran (THF) was treated with (0.0826 moles) n-butyllithium at room temperature. After 14.5 hours, 10.00 g (0.0825 moles) solid 6-(dimethylamino)fulvene were added to the orange-brown solution and the mixture was stirred at room temperature for 8.5 hours. The mixture was then reacted with 6.50 g (0.171 moles) $LiAlH_4$ and refluxed 15.5 hours. Then 0.0032 moles n-butyllithium was added and the mixture was stirred for 10 minutes. The mixture was hydrolysed with 500 g ice, 500 mL ether and 200 mL concentrated HCl. The aqueous phase was extracted 3 times with 300 mL ether. The ether extracts were combined and the ether evaporated. The solid residue was mixed with pentane and filtered over silica. The yield was 5.7 g (fluorenyl)(cyclopentadienyl)methane having a gas chromatographic purity of 98%.

Example 3

The cyclopentadienyl-type ligand, (fluorenyl)(cyclopentadienyl)(methyl)methane was prepared as follows. A solution of 5.0 g fluorene (0.030 mole) was treated with 0.030 mole n-butyllithium in 200 mL THF and stirred for two hours at room temperature. Then 0.030 mole 6-(dimethyl)aminofulvene was added and the mixture was stirred for five hours. The deep red solution was then reacted with 0.060 mole methyllithium and the mixture was refluxed for 8 to 10 hours to form a dianion. The reaction product was hydrolysed very slowly with cooling. The reaction vessel was cooled in a dry ice bath and the reaction mixture was hydrolysed by very slow dropping of a solution of aqueous HCl in THF. The thus produced CHMe-bridged ligand was extracted with pentane, dried over sodium sulfate, and the solvent was evaporated.

Example 4

The metallocene compound (fluorenyl)(cyclopentadienyl)methane zirconium dichloride was prepared by reacting 2.00 g (8.19 mmol) (fluorenyl)(cyclopentadienyl)methane prepared as described in example 1 and 16.38 mmol n-butyllithium in 100 mL ether at room temperature for 4 hours. Then 1.91 g (8.2 mmol) $ZrCl_4$ were added and the mixture was stirred at room temperature for 4 hours. A red precipitate formed which was filtered over sodium sulfate and washed with 50 ml ether. The solid was then extracted with 150 mL methylene chloride. Red crystals were recovered after adding 50 mL toluene, reducing the volume by half through evaporation and cooling.

That which is claimed is:

1. A process for preparing a cyclopentadienyl-type ligand comprising:
   (1) reacting an alkali metal salt of a cyclopentadienyl-type compound and an aminofulvene compound to form a monoanion,
      wherein said cyclopentadienyl-type compound is selected from the group consisting of unsubstituted cyclopentadiene, substituted cyclopentadiene, unsubstituted indene, substituted indene, unsubstituted fluorene, and substituted fluorene, wherein the substituents are selected from the group consisting of hydrocarbyl groups containing 1 to 12 carbon atoms, alkoxy groups containing 1 to 12 carbon atoms, and halide,
      wherein said aminofulvene compound is represented by the formula

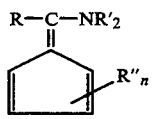

wherein R is an alkyl group containing 1 to 20 carbon atoms or hydrogen, wherein each R' is individually selected from alkyl groups containing 1 to 20 carbon atoms, and each R" is individually selected from the group consisting of hydrocarbyl groups containing 1 to 20 carbon atoms, and n is 0 to 4;
   (2) reacting said monoanion and a reducing agent to form a dianion,
      wherein said reducing agent is selected from the group consisting of alkali metal compounds containing a hydrocarbyl group containing 1 to 20 carbon atoms, lithium aluminum hydride, and hydrogen; and
   (3) reacting said dianion and water to produce said cyclopentadienyl-type ligand.

2. A process according to claim 1 wherein R' and R" in said aminofulvene compound each contain 1 to 10 carbon atoms.

3. A process according to claim 2 wherein said aminofulvene compound is 6-(dimethylamino)fulvene.

4. A process according to claim 1 wherein said cyclopentadienyl-type compound is fluorene or a substituted fluorene.

5. A process according to claim 1 wherein said reducing agent is an alkali metal compound containing 1 to 10 carbon atoms.

6. A process according to claim 5 wherein said reducing agent is methyllithium, butyllithium, or phenyllithium.

7. A process according to claim 6 wherein said reducing agent is methyllithium.

8. A process according to claim 1 wherein said reacting in step (1) is conducted at a temperature in the range of from about 0° C. to about 150° C., said reacting in step (2) is conducted at a temperature in the range of from about 0° C. to about 200° C., and said reacting in step (3) is conducted at a temperature that does not exceed about 20° C.

9. A process according to claim 8 wherein said reacting in step (1) is conducted at a temperature in the range of from about 10° C. to about 100° C., said reacting in step (2) is conducted at a temperature in the range of from about 10° C. to about 150° C., and said reacting in step (3) is conducted at a temperature that does not exceed about 15° C.

10. A process according to claim 1 further comprising reacting said cyclopentadienyl-type ligand of step (3) and an alkali metal compound to form an isolated dianion,
    wherein said alkali metal compound contains a hydrocarbyl group containing 1 to 20 carbon atoms; and
    reacting said isolated dianion and a transition metal-containing compound to prepare a metallocene compound,
    wherein said transition metal-containing compound is represented by the formula $MX_x$, wherein M is a Group IVB or VB transition metal, x is the valence of the transition metal, and each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydrogen.

11. A process according to claim 10 wherein said transition metal is selected from the group consisting of zirconium, hafnium, titanium, and vanadium.

12. A process according to claim 11 wherein said transition metal is zirconium or hafnium.

13. A process according to claim 10 wherein X is a halide.

14. A process according to claim 10 wherein said transition metal-containing compound is zirconium tetrachloride.

15. A process for preparing a metallocene compound comprising:
    (1) reacting an alkali metal salt of a cyclopentadienyl-type compound and an aminofulvene compound to form a monoanion,
       wherein said cyclopentadienyl-type compound is selected from the group consisting of unsubstituted cyclopentadiene, substituted cyclopentadiene, unsubstituted indene, substituted indene, unsubstituted fluorene, and substituted fluorene, wherein the substituents are selected from the group consisting of hydrocarbyl groups containing 1 to 12 carbon atoms, alkoxy groups containing 1 to 12 carbon atoms, and halide, wherein said aminofulvene compound is represented by the formula

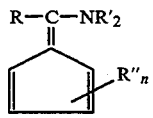

wherein R is an alkyl group containing 1 to 20 carbon atoms or hydrogen, wherein each R' is individually selected from alkyl groups containing 1 to 20 carbon atoms, and each R" is individually selected from the group consisting of hydrocarbyl groups containing 1 to 20 carbon atoms, and n is 0 to 4;

(2) reacting said monoanion and a reducing agent to form a dianion,
wherein said reducing agent is selected from the group consisting of alkali metal compounds containing a hydrocarbyl group containing 1 to 20 carbon atoms and hydrogen; and (3) reacting said dianion and a transition metal-containing compound to form said metallocene compound,
wherein said transition-metal containing compound is represented by the formula $MX_x$, wherein M is a Group IVB or VB transition metal, x is the valence of the transition metal, and each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydrogen.

16. A process for preparing a cyclopentadienyl-type ligand said process consisting essentially of:
(1) reacting an alkali metal salt of a cyclopentadienyl-type compound and an aminofulvene compound to form a monoanion,
wherein said cyclopentadienyl-type compound is selected from the group consisting of unsubstituted cyclopentadiene, substituted cyclopentadiene, unsubstituted indene, substituted indene, unsubstituted fluorene, and substituted fluorene, wherein the substituents are selected from the group consisting of hydrocarbyl groups containing 1 to 12 carbon atoms, alkoxy groups containing 1 to 12 carbon atoms, and halide,
wherein said aminofulvene compound is represented by the formula

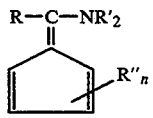

wherein R is an alkyl group containing 1 to 20 carbon atoms or hydrogen, wherein each R' is individually selected from alkyl groups containing 1 to 20 carbon atoms, and each R" is individually selected from the group consisting of hydrocarbyl groups containing 1 to 20 carbon atoms, and n is 0 to 4;

(2) reacting said monoanion and a reducing agent to form a dianion,
wherein said reducing agent is selected from the group consisting of alkali metal compounds containing a hydrocarbyl group containing 1 to 20 carbon atoms, lithium aluminum hydride, and hydrogen; and (3) reacting said dianion and water to produce said cyclopentadienyl-type ligand.

17. A process for preparing a metallocene compound said process consisting essentially of:
(1) reacting an alkali metal salt of a cyclopentadienyl-type compound and an aminofulvene compound to form a monoanion,
wherein said cyclopentadienyl-type compound is selected from the group consisting of unsubstituted cyclopentadiene, substituted cyclopentadiene, unsubstituted indene, substituted indene, unsubstituted fluorene, and substituted fluorene, wherein the substituents are selected from the group consisting of hydrocarbyl groups containing 1 to 12 carbon atoms, alkoxy groups containing 1 to 12 carbon atoms, and halide,
wherein said aminofulvene compound is represented by the formula

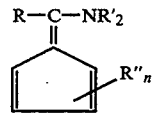

wherein R is an alkyl group containing 1 to 20 carbon atoms or hydrogen, wherein each R' is individually selected from alkyl groups containing 1 to 20 carbon atoms, and each R" is individually selected from the group consisting of hydrocarbyl groups containing 1 to 20 carbon atoms, and n is 0 to 4;

(2) reacting said monoanion and a reducing agent to form a dianion,
wherein said reducing agent is selected from the group consisting of alkali metal compounds containing a hydrocarbyl group containing 1 to 20 carbon atoms and hydrogen; and (3) reacting said dianion and a transition metal-containing compound to form said metallocene compound,
wherein said transition-metal containing compound is represented by the formula $MX_x$, wherein M is a Group IVB or VB transition metal, x is the valence of the transition metal, and each X is individually selected from the group consisting of hydrocarbyl groups containing 1 to 12 carbon atoms, alkoxy groups containing 1 to 12 carbon atoms, aryloxy groups containing 6 to 12 carbon atoms, halide and hydrogen.

* * * * *